United States Patent [19]

Hillman

[11] 4,443,637

[45] Apr. 17, 1984

[54] THERMOCHEMICAL CONVERSION OF BIOMASS TO ETHANOL

[75] Inventor: Melville E. D. Hillman, Columbus, Ohio

[73] Assignee: Battelle Development Corporation, Columbus, Ohio

[21] Appl. No.: 389,414

[22] Filed: Jun. 17, 1982

[51] Int. Cl.³ .............................................. C07C 29/00
[52] U.S. Cl. .................................. 568/876; 568/878; 568/852
[58] Field of Search ................................ 568/876, 878

[56] References Cited

U.S. PATENT DOCUMENTS 2,177,557  10/1939  Bergstrom et al. ..................... 202/5

Primary Examiner—J. E. Evans
Attorney, Agent, or Firm—Mueller and Smith

[57] ABSTRACT

Disclosed is a process for converting a carbohydrate or lactic acid feedstock into an ethanol product in the presence of a metal salt at a reaction temperature ranging from about 250° to about 400° C. The improvement comprises establishing a reaction mixture of said feedstock, said metal salt, water, and an organic solvent. The organic solvent has a boiling point above about 150° C., is stable at the reaction temperature, and solvates said feedstock. The solvent is selected from the group consisting of an alcohol, an ether, a tertiary amine, an amine oxide, a quaternary ammonium hydroxide, and a sulfoxide.

20 Claims, No Drawings

THERMOCHEMICAL CONVERSION OF BIOMASS TO ETHANOL

CROSS REFERENCE TO RELATED APPLICATIONS

This application is cross-referenced to commonly assigned application U.S. Ser. No. 144,190, of Hillman et al., entitled "Gasohol Production from Thermochemical Conversion of Biomass to Ethanol;" U.S. Ser. No. 144,189, of Hillman, entitled "One-Step Catalytic Thermochemical Conversion of Biomass to Ethanol;" and U.S. Ser. No. 144,194, of Hillman et al. entitled "Multi-Step Thermochemical Conversion of Biomass to Ethanol," said applications all having been filed on Apr. 28, 1980.

BACKGROUND OF THE INVENTION

The present invention relates to the synthesis of ethanol from biomass and more particularly to a much improved synthesis by a catalytic thermochemical process.

Conversion of biomass to ethanol by fermentation techniques is a well practiced process, especially with the emerging importance of gasohol in today's economy. Conventional fermentation techniques, however, suffer from a number of drawbacks including, for example, protracted reaction times, the need for sterile reaction conditions, the need for purified feedstocks, the production of voluminous by-products, and an energy intensive distillation operation for recovery of ethanol from water. The need for an alternate route for converting biomass to ethanol thus exists. Unfortunately, no alternative process has emerged in the marketplace.

Related application U.S. Ser. No. 144,189 discloses a method for thermochemically converting a sacchariferous material into ethanol wherein a reaction mixture comprising water, said sacchariferous material, and a metallic salt is heated under reaction conditions of a temperature of between 150° and 400° C., a pressure of at least atmospheric, and for a time adequate for directly forming ethanol and a metallic oxide or hydroxide. The metal of the metallic salt is restricted to a metal whose metallic carbonate formed in the reaction zone decomposes under the reaction conditions to generate the metallic oxide or hydroxide in situ. Related application U.S. Ser. No. 144,190 discloses a method for making a liquid fuel-ethanol blend which comprises establishing an aqueous reaction mixture of the carbohydrate material, a metal salt, and water in a reaction zone held at elevated temperature of about 150° C. to 300° C. to form an intermediate carbohydrate complex of said metal and/or a metal lactate salt. The complex and/or lactate salt then is pyrolyzed at a temperature of about 275° to 400° C. in the presence of water in a pyrolysis zone to form ethanol. The ethanol is recovered and then blended with a combustible liquid fuel. Related application U.S. Ser. No. 144,194 discloses a method for making ethanol from a carbohydrate material wherein an aqueous reaction mixture of a carbohydrate material, water, and a metal salt are heated at elevated temperature to produce an intermediate complex and/or lactate salt which is separated from the reaction mixture. The separated complex and/or lactate salt and water then are admitted into a pyrolysis zone held at a temperature ranging from between about 250° and 400° C. to pyrolyze the complex and/or salt to form ethanol. The proportion of water in said zone is restricted to be not in substantial excess of that proportion required for formation of ethanol and by-product metallic carbonate.

While the foregoing thermochemical processes are a significant advance in the art, yields of ethanol generally are only a few percent of the theoretical proportion of ethanol that could be made. Thus, there is a need for improving the foregoing thermochemical processes so that the yields of ethanol are substantially increased. Moreover, the product mixture obtained by the above-described thermochemical processes contains many by-products in very minor proportions. Thus, there exists a need for suppressing by-product formation in such thermochemical processes. The present invention is addressed to solving these problems as well as providing numerous additional distinct advantages in the thermochemical process.

BROAD STATEMENT OF THE INVENTION

The present invention is a method for converting a feedstock selected from a carbohydrate, a metallic salt of lactic acid, and mixtures thereof, into an ethanol product at a reaction temperature ranging from about 250° C. to about 400° C. The improvement in such process comprises establishing a reaction mixture of said feedstock, water, and a solvent having a boiling point above about 150° C., and preferably above about 200° C. and selected from the group consisting of an alcohol, an ether, a tertiary amine, an amine oxide, a sulfoxide, a quaternary ammonium hydroxide and mixtures thereof. The solvent, preferably of low volatility (high boiling), solvates the feedstock and is stable at the reaction temperature and at the reaction pressure of the process. The pressure maintained during the process ranges from atmospheric to autogenous pressure. The amount of solvent in said reaction (water-solvent) mixture ranges from about 10% to about 98% by weight.

Advantages of the present invention include the ability to thermochemically convert the feedstock to ethanol at atmospheric pressure. Another advantage is that much higher yields are obtained by use of the organic solvents disclosed herein then are obtained by using water alone as the solvent. Another distinct advantage is that greater than about 95% of the feedstock is converted in the process. Yet another advantage is that the by-products produced in the process essentially have been reduced to but one or two by-products, which means recovery of a pure ethanol product is greatly facilitated. A further advantage is that low proportions of water are required in the process for producing the ethanol which additionally contributes to a purer (dryer) ethanol product. These and other advantages readily will be apparent to those skilled in the art based upon the disclosure contained herein.

DETAILED DESCRIPTION OF THE INVENTION

Solvents suitable for use in the present invention should meet or exceed certain requirements in order to be adjudged useful. These requirements include, for example, the ability to solvate preferable feedstocks including simple sugars and metal lactate salts, be thermally stable at the reaction temperature which may be up to about 300° C., be hydrolytically stable in the presence of water, be stable in the presence of bases including barium hydroxide or calcium carbonate, for example, not neutralize the basic metal salt catalyst in the process, not react with feedstock to form side-products, and the like. Thus, solvency of the feedstock and stability under reaction conditions are prime requirements which the solvent must meet. The classes of solvents useful in the process, then, typically will be highly polar and of low volatility (probably high boiling) and most preferably will be multi-functional. The classes of solvents determined to effectively operate in the process include alcohols, ethers, tertiary-amines, amine oxides, sulfoxides, and certain quaternary ammonium hydroxides. Necessarily, not all chemical compounds within such classes of compounds will be suitable for use in the process of the present invention, though those compounds meeting the requirements set forth above generally will function adequately in the process.

Referring to alcohol solvents, the alcohol solvents must be stable at reaction conditions of temperature and pressure. Alcohol solvents suitable for use in the present process include, for example, pentaerythritol, trimethylol propane, trimethylol butane, glycol, and the like. Such alcohols have high boiling points and are not readily susceptible to dehydration or other degradation under the elevated reaction temperatures of the present invention. Also, some of the alcohol solvents suitable for the invention contain an ether group and may be preferred since they contain a combination of functionalities determined to be useful for the solvents of the present invention.

Aside from the alcohol ethers enumerated above, additional ether solvents useful in the present invention include diglyme (diethylene glycol dimethyl ether), tetrahydrofuran, tetrahydropyran, dioxane, and Cellosolves (e.g. ethylene glycol monoalkyl ether).

Tertiary-amines useful in the present invention preferably will be heterocyclic or aromatic in nature in order to provide the requisite stability at the elevated reaction temperatures. Suitable amines include, for example, N-methyl piperidine, N,N-dimethyl piperazine, N-methyl morpholine, dimethyl-cyclohexyl amine, pyridine, pyrimidine, tetrazine, quinoline, quinazoline, triethylene diamine, triethanol amine, and the like. It readily will be apparent to those skilled in the art that additional tertiary-amine compounds suitably may function in the process of the present invention also.

Many of the foregoing tertiary-amines can be formed into amine oxides which may find use in the present invention. Additional amine oxides include, for example, triethanol amine oxide, pyridine amine oxide, trimethyl amine oxide, and the like. Desirably long chain aliphatic groups are not attached to the amine oxides as the solvent would not have sufficient polarity to be useful in the process. That is, while the solvent must be liquid under operating temperatures, a compound which melts, for example, at 250°–300° C. may not be entirely practical for use in the process as preheating of the solvent would be required; otherwise, the feedstock in dry form would be required to be stable during heating to such elevated temperature. The solvent should melt at a temperature not above about 200° C., preferably at less than about 150°–200° C.

Suitable sulfoxide solvents include dimethyl sulfoxide, tetramethylene sulfoxide, and similar $C_2$–$C_4$ alkyl sulfoxides. Quaternary ammonium hydroxides which may find advantageous use in the process include, for example, tetramethyl ammonium hydroxide, tetraphenyl ammonium hydroxide, N-methyl pyridinium hydroxide, and like quaternary ammonium hydroxides which are stable under the reaction conditions and which melt at a suitably low temperature to find practical utility in the process of the present invention.

It will be appreciated that additional solvents within the classes of solvents enumerated above additionally will find utility in the process of the present invention. Those solvents disclosed herein merely are representative of the solvents which can be used in the process. The proportion of solvent useful in the process generally will be between about 10% and 98% by weight of solvent and water in the reaction mixture. While water is a necessary reactant in the process, the proportion of water should not be too great as subsequent purification of the ethanol product would be encountered. Thus, it is preferred to operate the present process with less than 10% water with the remainder of the solvent being the organic solvent or combination organic solvents disclosed herein.

The lactic acid or lactate salt feedstock for the present invention can be made from a carbohydrate material, which also is a suitable feedstock, in accordance with the disclosures of the cross-referenced applications cited above. Additional methods for converting carbohydrate material to lactic acid can be found in Montgomery and Ronca, "Chemical Production of Lactic and Other Acids from Molasses," *Industrial and Engineering Chemistry*, Vol. 45, pp 1136–1147 (1953) and Holten, *Lactic Acid: Properties in Chemistry of Lactic Acid and Derivatives*, Verlag Chemie, GmbH, Copenhagen, Denmark, the disclosures of which are expressly incorporated herein by reference. Briefly, the production of lactic acid from carbohydrates, sugar, and the like, is accomplished by heating such material with an alkali metal, alkaline earth metal, or other metal hydroxide or oxide or carbonate, for example, at temperatures ranging from as low as about 25° C. (e.g. when using a barium base) up to 200° C. and higher. The art shows conversions to lactic acid up to 95% and higher are achievable without much difficulty. Also, lactic acid is commercially available from many sources.

The lactic acid, from whatever source derived, can be used in acid form in combination with a metal salt or the lactic acid metal salt can be performed in conventional fashion. The metal salts are catalytic in the process and, thus, their presence is necessary.

Suitable catalysts for use in the present invention are those metal salts that can display a basic reaction in an acidic environment. Preferable catalysts are oxides, hydroxides, and carbonates of alkali metals and alkaline earth metals. For present purposes, alkali metals include lithium, sodium, potassium, rubidium, and cesium and alkaline earth metals include beryllium, magnesium, calcium, strontium, and barium. Additional catalysts useful in the present invention include salts of amphoteric or transition metals such as salts of, for example, aluminum, zinc, lead, barium, cadmium, magnesium, mercury, silver, cobalt, manganese, bismuth, gallium, thorium, uranium, niobium, copper, iron, nickel, and the like, preferably provided as an oxide, hydroxide, or carbonate. Further suitable metallic salts include complex metallic salts which contain one metal plus either a second metal or a non-metal or other anion. Representative anions of such complex metallic salts, for example, can be selected from the following: arsenate, chromate, ferricyanide, carbonate, silicate, molybdate, (dibasic, tri-basic, pyro, meta, ortho) phospate, plumbite, sulfate, aluminate, bisulfite, (meta or tetra) borate, chlorate, chloraurate, chloroplatinate, dithionate, manganate, nitrite, selenate, (meta or ortho) silicate, stannate, sulfite, tartrate, thiocyanate, thiosulfate, tungstate, vanadate, and the like. Even more complex metallic salts such as salts of heteropolyacids (e.g. sodium salt of phosphomolybdic acid) may be useful in the process also. It should be recognized that combinations of such salts can be used as well as materials which generate the suitable salt in the reaction mixture in situ.

As previously noted based upon the chemical reaction steps involved in the process, metal oxides may be preferred for use in the process since metal oxides can be generated from the process for recycle thereto. Moreover, for continuous operation of the present invention selection of a metal whose carbonate decomposes to metal oxide and carbon dioxide gas under the reaction conditions prevailing in the pyrolysis zone may be desired for self-generating catalysts for the process. Such metal carbonates include, for example, zinc carbonate, copper carbonate (possibly complexed with $Cu(OH)_2$), cadmium carbonate, mercurous carbonate, silver (I) carbonate, cobalt (II) carbonate, iron (II) carbonate, thorium carbonate, uranium carbonate, manganese carbonate, nickel carbonate, and lead carbonate, which can be decomposed at the pyrolysis temperatures of the pyrolysis zone.

Suitable carbohydrate feedstock material for the present invention most often will be saccharides and often the term sugar will be used for their description. Simple monosaccharides for use in the present process include hexoses such as, for example, glucose, mannose, gallactose, gulose, formose, and fructose; pentoses such as, for example, arabinose, xylose, ribose, and rhamnose; tetroses such as, for example, erythrose and threose; and trioses such as, for example, glycerose. Derivatives of saccharides such as, for example, guconic acid, mono-, and diphosphatates of fructose, etc., also can be used in the process. It should be noted that conversion of pentose sugars (for example those derived from hemicellulose from wood hydrolysis) by the present process will result in the production of one mole of a lactate salt and probably one mole of a glycolate salt. The important consideration in the use of the pentose sugars is that they will not poison the reaction which occurs with conventional fermentation processes because of the effect of by-product furfuraldehyde.

Additional carbohydrate feedstock include disaccharides such as, for example, sucrose, maltose, and the like. Other suitable feedstock include polysaccharoses and oligosaccharides. Such sugars can be derived from sugar crops such as sugar cane, sugar beets, or sweet sorghum; or by the partial or complete hydrolysis of starch or starch-like materials in grains such as corn, wheat, oats, and the like; or can be derived from other crops such as potatoes, yams, manioc, and the like.

Additional sugars suitable as feedstock for the present invention can be derived from lignocellulosic materials such as agricultural and forestry residues including the non-lignin fraction of black liquor or by-products such as, for example, corn stalks or corn cobs, sawdust or other forest residues, bagasse, cattle or other manure, leaves, newspaper from municipal waste, and the like. Such agricultural and forestry residues are hydrolyzed or at least partially hydrolyzed to sugars or oligosaccharides prior to their admission to the present process. The present process also may utilize soluble polysaccharides such as, for example, soluble starch or polysaccharides that have been pretreated to reduce the degree of crystallinity (e.g. amorphous cellulose).

Thus, it can be seen that a myriad of materials can be used directly or converted into suitable feedstock for use in the present process. Such materials need not be rigorously purified for admission into the process as is required in conventional fermentation processes, because typical fermentation poisonous materials do not interfere with the thermochemical process of the present invention.

Reaction conditions for the present process include temperatures ranging from between about 250° to about 400° C. and desirably between about 275° and 325° C. The actual temperature employed in the process necessarily will depend upon the particular feedstock, metal salt, and solvent employed in the process. While elevated temperatures are required for the process, pressures desirably are maintained as low as possible in order to minimize expense of reactors required to house the reaction. Many of the solvents disclosed above permit atmospheric operation of the process which is a substantial step forward in the art. When superatmospheric pressure is employed, though, much improved yields of product ethanol are obtained. Elevated pressures, when employed, desirably are autogenous and generally range from about 500 to about 3,000 psig.

The process additionally may be conducted under an inert gas blanket or inert atmosphere. Suitable inert or non-reactive gases in the process include, for example, nitrogen, carbon dioxide, propane, argon, and the like and mixtures thereof.

The primary product of the present invention is ethanol and such ethanol generally will be in a dryer form than heretofore was possible. A distinct advantage in employing the organic solvents of the present invention is the reduction of the number of by-products in the process. While one of such by-products currently is of unknown structure, the examples will provide much analytical information concerning such unidentified compound. Of importance is the appreciation that the by-products have been reduced and readily are separable from the desired ethanol product.

In connection with the various operational modes which can be designed for the process, reference again is made to the three co-pending applications cited above. Materials of construction for the various zones are conventional for this type of high temperature, high pressure operation. Thus, where corrosion-resistant materials are required, use of austenitic stainless steel, plastic, glass-lined steel, wood, or even clay may be used. Concrete or steel can be used where corrosion or erosion is inconsequential. Piping, ductwork, and other appurtenant lines will be of similar material, conventionally constructed. It will be appreciated that various of the tanks, lines, reactors, and the like can be multiple, series, cascade, or parallel connected for additional treating time or capacity, for special effects.

The following examples show how the present invention has been practiced but should not be construed as limiting. In this application, all units are in the metric system and all proportions of product are expressed as a percentage of the theoretical proportion which could be made.

IN THE EXAMPLES

EXAMPLE 1

Lactic acid (89.9% lactic acid in water in Examples 1, 2, and 3), triethanolamine, solvent, and sodium hydroxide were heated in a round-bottom glass reactor fitted with a distillation head. Essentially atmospheric pressure prevailed during the entire run. Three control experiments also were conducted. The first control (Run No. 3) utilized triethanolamine solvent and sodium hydroxide as the only reactants. The second control (Runs Nos. 21 and 23) utilized triethanolamine and lactic acid as the only reactants. The third control (Run No. C) utilized calcium lactate and water as the only reactants. The reaction conditions and results obtained appear below.

TABLE 1

| Run No. | Reactants Ingredients | wt (g) | Temp. (°C.) | Yield of Ethanol (% of theoretical) |
|---|---|---|---|---|
| 73 | Triethanolamine | 244.8 | 248° | 11.5 |
|  | Lactic acid | 75.7 |  |  |
|  | Sodium hydroxide | 60.8 |  |  |
| 3 | Triethanolamine | 257.9 | 200° | Trace |
|  | Sodium hydroxide | 15.0 |  |  |
| 21 | Triethanolamine | 153.4 | 210° | 0 |
|  | Lactic acid | 320.4 |  |  |
| 23 | Triethanolamine | 232.6 | 227° | 0.27 |
|  | Lactic acid | 97.4 |  |  |
|  | Water | 50.0 | 100° | 0 |
|  | Calcium lactate | 15.0 |  |  |

The above-tabulated results demonstrate the remarkable improvements in yields of ethanol at atmospheric pressure which are realized by conducting the reaction in the organic solvent. Also, the necessity for inclusion of a metal salt of lactic acid as the reactant for forming ethanol is demonstrated.

EXAMPLE 2

The procedure of Example 1 was repeated with N-methyldiethanolamine solvent, lactic acid, and sodium hydroxide. The control experiment deleted the lactic acid. Again, atmospheric pressure was maintained during the runs with the following results.

TABLE 2

| Run No. | Reactants Ingredients | wt (g) | Temp. (°C.) | Yield of Ethanol (% of theoretical) |
|---|---|---|---|---|
| 74 | N—methyldiethanolamine | 281.0 | 235° | 10.3 |
|  | Lactic acid | 79.1 |  |  |
|  | Sodium hydroxide | 63.2 |  |  |
| 4 | N—methyldiethanolamine | 188.7 | 205° | Trace |
|  | Sodium hydroxide | 15.0 |  |  |

Again, the unexpected yield of ethanol at atmospheric pressure is demonstrated in the organic solvent.

EXAMPLE 3

Calcium lactate pentahydrate was mixed with water followed by the addition of triethanolamine solvent to bring the total volume of the mixture to 1500 ml. The mixture was heated with stirring to dissolve the calcium lactate. The mixture then was placed in a high pressure autoclave with continuous stirring and the mixture heated to 289° C. over a 5 hour period. The temperature of the mixture then was maintained between 289° and 270° for an additional 1 hour. Samples were removed periodically during and after the heat up for analysis.

The product reaction mixture analyzed to contain less than 5% unreacted calcium lactate. Only three reaction products were evident: ethanol (about 6% of theoretical), an unidentified product (about 30%), and butanediol (about 4%). The precise composition of the unidentified product is unknown currently, though it is known to be a non-nitrogen organic compound with an even number molecular weight of apparently 104 or 106. The unidentified product is a polyol, most likely a $C_4$ triol or $C_4$ diol ether, or a $C_5$ diol.

These results should be compared to the pyrolysis of calcium lactate pentahydrate (75 g), calcium hydroxide (35 g), and water (890 g) at 301° and 1200 psig wherein 0.87% ethanol was made. The unexpected improved yields and fewer by-products produced using the organic solvent is demonstrated.

The amount of ethanol product reported in this example and in Example 4 has been corrected for the apparent appearance of ethanol from degradation of the triethanolamine solvent at the elevated temperatures and pressures reported.

EXAMPLE 4

The procedure of Example 3 was repeated with calcium lactate pentahydrate (180 g), distilled water (100 ml), and triethanolamine (to 1000 ml total volume of mixture). Two hours were required to heat the reaction mixture to 293° C. after which the temperature was maintained at 286°–315° C. for an additional 2.5 hours. The only detectable products were ethanol (about 23% of theoretical), the unknown product and butanediol described in Example 3.

I claim:

1. In a process for converting a feedstock selected from the group consisting of a carbohydrate, lactic acid, and mixtures thereof, into product ethanol in the presence of a metal salt at a reaction temperature ranging from about 250° to about 400° C., the improvement which comprises:
  establishing a reaction mixture of said feedstock, said metal salt, water, and an organic solvent which has a boiling point of at least about 150° C., can solvate said feedstock, and is stable at said reaction temperature, said solvent selected from the group consisting of an alcohol, an ether, a tertiary amine, an amine oxide, a sulfoxide, a quaternary ammonium hydroxide, and mixtures thereof, the proportion of solvent in said reaction mixture ranging from between about 10% and about 95% by weight of said water and said organic solvent, said process being conducted at atmospheric pressure.

2. The process of claim 1 wherein said organic solvent is selected from the group consisting of glycerol, pentaerythritol, trimethylolpropane, diglyme, N-methyl piperidine, N,N'-dimethyl piperazine, N-methyl morpholine, dimethyl-cyclohexyl amine, tetrahydrofuran, pyridine, pyrimidine, tetrazine, quinoline, quinazoline, tetrahydro thiophene, triethylene diamine, triethanolamine, triethanolamine oxide, pyridine amine oxide, trimethylamine oxide, dimethyl sulfoxide, tetramethylene sulfoxide, tetramethyl ammonium hydroxide, tetraphenyl ammonium hydroxide, N-methyl pyridinium hydroxide, and mixtures thereof.

3. The process of claim 1 wherein said metal salt and said lactic acid are preformed into a metallic salt of lactic acid prior to said establishing said reaction mixture.

4. The process of claim 1 wherein said carbohydrate feedstock is a sacchariferous material.

5. The process of claim 1 wherein said reaction temperature ranges from about 275° to 325° C.

6. The process of claim 4 wherein said sacchariferous material comprises hydrolysis products of lignocellulosic material.

7. The process of claim 1 wherein said metal salt is a metal hydroxide, oxide, or carbonate.

8. The process of claim 7 wherein said metal of said metal salt is selected from the group consisting of calcium, sodium, magnesium, aluminum, zinc, lead, barium, cadmium, magnesium, mercury, silver, cobalt, manganese, copper, iron, nickel, and mixtures thereof.

9. In a process for converting a feedstock selected from the group consisting of a carbohydrate, lactic acid, and mixtures thereof, into product ethanol in the presence of a metal salt at a reaction temperature ranging from about 250° to about 400° C., the improvement which comprises:

establishing a reaction mixture of said feedstock, said metal salt, water, and an organic solvent which has a boiling point of at least about 150° C., can solvate said feedstock, and is stable at said reaction temperature, said solvent selected from the group consisting of glycerol, pentaerythritol, trimethylolpropane, diglyme, N-methyl piperidine, N,N'-dimethyl piperazine, N-methyl morpholine, dimethyl-cyclohexyl amine, tetrahydrofuran, pyridine, pyrimidine, tetrazine, quinoline, quinazoline, tetrahydro thiophene, triethylene diamine, triethanolamine, triethanolamine oxide, pyridine amine oxide, trimethylamine oxide, dimethyl sulfoxide, tetramethylene sulfoxide, tetramethyl ammonium hydroxide, tetraphenyl ammonium hydroxide, N-methyl pyridinium hydroxide, and mixtures thereof, the proportion of solvent in said reaction mixture ranging from between about 10% and about 95% by weight of said water and said organic solvent.

10. The process of claim 9 wherein said process is conducted at autogenous pressure.

11. The process of claim 9 wherein said metal salt and said lactic acid are preformed into a metallic salt of lactic acid prior to said establishing said reaction mixture.

12. The process of claim 9 wherein said carbohydrate feedstock is sacchariferous material.

13. The process of claim 9 wherein said reaction temperature ranges from about 275° to 325° C.

14. The process of claim 12 wherein said sacchariferous material comprises hydrolysis products of lignocelulosic material.

15. The process of claim 9 wherein said metal salt is a metal hydroxide, oxide, or carbonate.

16. The process of claim 9 wherein said metal salt is selected from the group consisting of calcium, sodium, magnesium, aluminum, zinc, lead, barium, cadmium, mercury, silver, cobalt, manganese, copper, iron, nickel, and mixtures thereof.

17. In a process for converting a lactic acid feedstock into product ethanol in the presence of a metal salt at a reaction temperature ranging from about 250° to about 400° C., the improvement which comprises:

forming said lactic acid into a metallic salt thereof; and establishing a reaction mixture of said metallic salt of lactic acid, water, and an organic solvent which has a boiling point at least about 150° C., can solvate said metallic salt of lactic acid and is stable at said reaction temperature, said solvent selected from the group consisting of an alcohol, an ether, a tertiary amine, an amine oxide, a sulfoxide, a quaternary ammonium hydroxide, and mixtures thereof, the proportion of solvent in said reaction mixture ranging from between about 10% and about 95% by weight of said water and said organic solvent.

18. The process of claim 17 wherein said process is conducted at autogenous pressure.

19. The process of claim 17 wherein said reaction temperature ranges from about 275° to 325° C.

20. The process of claim 17 wherein said metal salt is a metal hydroxide, oxide, or carbonate, and said metal of said metal salt is selected from the group consisting of calcium, sodium, aluminum, zinc, lead, barium, cadmium, magnesium, mercury, silver, cobalt, manganese, copper, iron, nickel, and mixtures thereof.

* * * * *